United States Patent
Gadd et al.

(10) Patent No.: US 9,187,468 B2
(45) Date of Patent: Nov. 17, 2015

(54) TOPICAL OCULAR ANALGESIC AGENTS

(71) Applicant: Novartis AG, Basel (CH)

(72) Inventors: Martha E. Gadd, Fort Worth, TX (US);
Peter G. Klimko, Fort Worth, TX (US);
Karen C. David, Mansfield, TX (US);
Kenneth C. Appell, Burleson, TX (US);
Mark R. Hellberg, Needham, MA (US)

(73) Assignee: NOVARTIS AG (CH)

( * ) Notice: Subject to any disclaimer, the term of this patent is extended or adjusted under 35 U.S.C. 154(b) by 0 days.

(21) Appl. No.: 14/179,932

(22) Filed: Feb. 13, 2014

(65) Prior Publication Data

US 2014/0228338 A1    Aug. 14, 2014

Related U.S. Application Data

(60) Provisional application No. 61/764,166, filed on Feb. 13, 2013.

(51) Int. Cl.

| | |
|---|---|
| *A61K 31/53* | (2006.01) |
| *A01N 43/66* | (2006.01) |
| *C07D 417/14* | (2006.01) |
| *C07D 401/04* | (2006.01) |
| *C07D 403/04* | (2006.01) |
| *A61K 9/00* | (2006.01) |
| *A61K 47/40* | (2006.01) |
| *C07D 251/16* | (2006.01) |
| *C07D 251/18* | (2006.01) |
| *A61K 47/32* | (2006.01) |

(52) U.S. Cl.
CPC ............ *C07D 417/14* (2013.01); *A61K 9/0048* (2013.01); *A61K 31/53* (2013.01); *A61K 47/40* (2013.01); *C07D 251/16* (2013.01); *C07D 251/18* (2013.01); *C07D 401/04* (2013.01); *C07D 403/04* (2013.01); *A61K 47/32* (2013.01)

(58) Field of Classification Search
CPC ....... A61K 31/53; A61K 47/32; A61K 47/40; A61K 9/0048; C07D 251/16; C07D 251/18; C07D 401/04; C07D 403/04; C07D 417/14
USPC ............................................... 514/210.2, 245
See application file for complete search history.

(56) References Cited

FOREIGN PATENT DOCUMENTS

| | | |
|---|---|---|
| WO | 2010/022055 A2 | 2/2010 |
| WO | 2011/103196 A | 8/2011 |

OTHER PUBLICATIONS

Bregman et al., "Identification of a potent, state-dependent inhibitor of Nav 1.7 with oral efficacy in the formalin model of persistent pain", Journal of Medicinal Chemistry, 2011, p. 4427-4445, vol. 54.
Chakka et al., "Discovery and hit-to-lead optimization of pyrrolopyrimidines as potent, state-dependent Nav1.7 antagonists", Bioorganic Medicinal Chemistry Letters, 2012, p. 2052-2062, vol. 22(5).
Chowdhury et al., "Discovery of XEN907, a spirooxindole blocker of Nav1.7 for the treatment of pain", Bioorganic Medicinal Chemistry Letters, 2011, p. 3676-3681, vol. 21(12).
Cox et al., "An SCN9A channelopathy causes congenital inability to experience pain", Nature, 2006, p. 894-898, vol. 444.
Fertleman et al., "SCN9A Mutations in Paroxysmal Extreme Pain Disorder: Allelic Variants Underlie Distinct Channel Defects and Phenotypes", Neuron, 2006, p. 767-774, vol. 52.
Tyagarajan et al., "Substituted biaryl oxazoles, imidazoles, and thiazoles as sodium channel blockers", Bioorganic and Medicinal Chemistry Letters, 2010, p. 5536-5540, vol. 20(18).
Zheng et al., Discovery of INCB10820/PF-4178903, a potent, selective, and orally bioavailable dual CCR2 and CCR5 antagonist, Bioorganic Medicinal Chemistry Letters, 2011, p. 1442-1446, vol. 21(5).

*Primary Examiner* — My-Chau T Tran (57) ABSTRACT

The topical ophthalmic use of certain 2,4-diamino-substituted 1,3-triazines for preventing or alleviating ocular pain in patients is disclosed. Topical ocular pharmaceutical composition are also disclosed.

12 Claims, 6 Drawing Sheets

FIG. 1

Formalin Blink Test for Topical Compound 1

FIG. 2

Cochet:Bonnet Esthesiometry Test for Topical Compound 1

FIG. 3

Formalin Blink Test for Topical Compound A

FIG. 4

Formalin Blink Test for Topical Compound B

FIG. 5

Formalin Blink Test for Topical Compound C

FIG. 6

Cochet:Bonnet Esthesiometry Test for Topical Compound C

TOPICAL OCULAR ANALGESIC AGENTS

The present application claims priority to U.S. Provisional Application Ser. No. 61/764,166, filed on Feb. 13, 2013, the disclosure of which is specifically incorporated by reference herein.

FIELD OF THE INVENTION

The present invention is directed to compounds and methods for use as topical ocular analgesic agents. In particular embodiments, the present invention is directed to the use of certain 2,4-diamino-substituted 1,3-triazines as topical ocular analgesic agents.

BACKGROUND

Pain is a perceived nociceptive response to local stimuli in the body. The perception of pain at the level of the central nervous system requires the transmission of painful stimuli by peripheral sensory nerve fibers. Upon stimulation of tissue (i.e., thermal, mechanical or chemical), electro-chemical signals are transmitted from the sensory nerve endings to the spinal column, and hence to the brain where pain is perceived.

Ocular pain can be co-incident with a number of conditions, including but not limited to trauma due to accidental or surgical injury, uveitis, dry eye, and diabetic neuropathy. The standard of care for treatment of ocular pain is typically either topically administered non-steroidal anti-inflammatory drugs (NSAIDs), or orally administered analgesic agents, such as NSAIDS or opioids like hydrocodone. These treatments suffer from limited efficacy and systemic and ocular side-effects. The use of topical ocular anesthetic agents is limited to physician settings, since patient-administered anesthetic regimens can lead to dry eye (due to the interruption of the neuronally-supported tear production feedback loop), possible impairment of wound healing, and corneal abrasion (due to the patient being unable to detect corneal injury).

Local anesthetics are another class of pain modulators that relieve pain by directly inhibiting nerve cellular function. One problem with local anesthetic therapy is that the anesthetics exhibit a short duration of action. Another problem with the use of local anesthetics is that their mechanism of action, non-specific membrane stabilization, can have the undesired coincident effect of also inhibiting biological functions of other cells, such as fibroblasts and surrounding neural cells. Therefore, even though pain sensation can be abated with local anesthetic treatment, healing and normal function of the tissue may be significantly compromised. There is a need, therefore, to discover agents which potently and specifically inhibit the transmission of painful stimuli by sensory afferents, without local anesthetic activity, following topical ocular application.

In addition to treating ocular pain, local topical ocular application of anesthetics has been proposed to reduce or eliminate sensations on the ocular surface to treat the symptoms of dry eye. However, chronic use of local anesthetics is accompanied by toxic side effects.

Consequently, there is a need for effective topical ocular agents that provide analgesic effects without causing anesthetic effects.

SUMMARY OF THE INVENTION

The invention provides compositions and methods for the treatment of ocular pain. In a particular aspect, a 2,4-diamino-substituted 1,3-triazine is administered to a patient in need thereof to prevent or alleviate pain in an eye without causing an anesthetic effect.

A 2,4-diamino-substituted 1,3-triazine is preferably administered topically to the eye.

Specific preferred embodiments of the invention will become evident from the following more detailed description of certain preferred embodiments and the claims.

DETAILED DESCRIPTION OF THE INVENTION

Unless indicated otherwise, all component amounts are presented on a % (w/v) basis.

In certain embodiments, the invention provides topically-active analgesic compounds for use in the eye that have increased efficacy and fewer systemic side-effects than orally administered analgesics. By lacking anesthetic effects at analgesically-effective doses, these compounds also reduce the risk of dry eye induction and corneal abrasion that is observed with local ocular anesthetics.

In a particular embodiment, the invention provides a method of treating ocular pain in a subject in need thereof. In certain embodiments, the subject is a human or non-human that has or is at risk of ocular pain associated with some condition. Such conditions include, but are not limited to, trauma due to accidental injury or surgical injury (such as postoperative photorefractive keratectomy (PRK) surgery), uveitis, dry eye, and diabetic neuropathy. Thus, the invention provides methods for treating or preventing ocular pain in patients having one or more of such conditions.

Methods and compositions of the invention comprise an ophthalmically acceptable carrier and at least one compound of Formula I:

I wherein:

Y=CH or N;
n=0 or 1, with the proviso that n=0 if Y=N;
X=a direct bond or $CH_2$;
Z=a phenyl or heteroatomic group, optionally substituted with phenyl, methyl; halo, trihalomethyl, or trihalomethoxy; and
$R^2$=H, Me, or F, with the Me or F groups in the 2 or 6 positions on the acetamide-bearing phenyl ring.

Among the preferred compounds of the present invention are the compounds 1-10 below:

1

-continued

2

3

4

5

6

7

8

9

II benzamide

10

Compounds of Formula I can be synthesized, for example, by methods described in: WO 2010 022055A2. Compound 1, for example, can be synthesized as described in *J. Med. Chem.* 2011, 54(13), 4427-4445.

Compared with orally administered analgesics, the topically-active compounds of the invention have increased efficacy and fewer systemic side-effects. In addition, the compounds of the invention lack anesthetic effects at analgesically-effective doses, thereby substantially reducing the risk of dry eye induction and corneal abrasion that can occur with ocular anesthetics.

Compounds 1-9 are known in the art; see *Journal of Medicinal Chemistry* 2011, 54(13), 4427-4445 (compound 1, disclosed as compound 52 in the paper) and WO 2010 022055A2 (compounds 1-9, disclosed therein as compounds T-I-: 338, 12, 464, 484, 571, 761, 770, 526, and 26, respectively).

In a preferred embodiment, the compound of Formula I used in a method of the invention is Compound 1.

2,4-diamino-substituted 1,3-triazines of the present invention are sodium channel 1.7 (Nav 1.7) inhibitors.

Sodium channel 1.7 (Nav 1.7) function has been implicated as necessary for pain sensation by human genetics studies. Patients with loss-of-function mutations are unable to perceive painful stimuli such as burns and bone breaks (see for example Cox et al., *Nature* 2006, 444, 894-898). Meanwhile, patients with gain-of-function mutations leading to increased channel opening suffer from severe chronic pain (see for example Fertleman et al., *Neuron* 2006, 52, 767-774).

Compounds of Formula I have been disclosed as Nav 1.7 antagonists with analgesic activity in experimental rat models of pain, when orally dosed; see *Journal of Medicinal Chemistry* 2011, 54(13), 4427-4445; and WO 2010 022055A2. Nav 1.7 blockers with a "reverse amide"/acetamide-to-benzamide switch from claimed compounds I, as for example II, are disclosed in WO11103196A, as is their use for treatment of eye inflammation. However, the use of either compound class of these compounds as topical ocular analgesics to treat ocular pain has not been disclosed or suggested.

In certain embodiments, the invention provides topical ocular pharmaceutical composition comprising at least one compound of Formula I that is administered in an ophthalmically acceptable carrier for topical ophthalmic administration. The compositions are formulated in accordance with methods known in the art. The compositions may contain more than one compound of Formula I. Additionally, the compositions may contain a second drug, other than a compound of Formula I. The compositions are formulated in accordance with methods known in the art for the particular route of administration desired.

In a preferred embodiment, a composition of the invention comprises a cyclodextrin or sodium polystyrene sulfonate.

The compositions administered according to methods of the invention contain an ophthalmically effective amount of a compound of formula I. As used herein, "an ophthalmically effective amount" means an amount sufficient to prevent or alleviate ocular pain. Generally, the compositions of the present invention will contain from 0.01% to 3% of a compound of Formula I. Preferably, the compositions of the present invention will contain from 0.1% to 1% of a compound of Formula I.

Preferably, the compositions administered according to the present invention will be formulated as solutions, suspensions and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions.

The compositions administered according to the present invention may also include various other ingredients, including but not limited to surfactants, tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm).

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 5.5-8.

Other compounds designed to lubricate, "wet," approximate the consistency of endogenous tears, aid in natural tear build-up, or otherwise provide temporary relief of dry eye symptoms and conditions upon ocular administration to the eye are known in the art and may be included in the compositions of the present invention. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Topical ophthalmic products are typically packaged in multidose form. Preservatives are typically required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or is other agents known to those skilled in the art. Such preservatives are typically employed at a level of from 0.001 to 1.0% w/v. Unit dose compositions of the present invention will be sterile, but typically will not contain a preservative and will be unpreserved.

Unless otherwise required by context, singular terms used herein shall include pluralities and plural terms shall include the singular.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Analgesic Effect of Compound 1 of Formula I as Compared to Other Nav 1.7 Inhibitors

Formalin Blink Test

Formalin was prepared at 0.1% final in 0.9% saline from a stock of 10% neutral buffered formalin (Sigma-Aldrich, St. Louis, Mo.). Compound 1 was selected as a test agent of formula I. Compounds A, B, and C were selected as comparator Nav 1.7 inhibitors known in the art. Compound A is also known in the literature as XEN907, and has been reported as a Nav 1.7 channel inhibitor with an $IC_{50}$ value of 3 nM in a guanidinium flux assay (Chowdhury, et al., *Bioorganic and Medicinal Chemistry Letters* 2011, 21(12), 3676-3681). The structure of Compound A is.

compound A

Compound B has been reported as a Nav 1.7 channel blocker with an $IC_{50}$ value of 15 nM in a whole-cell voltage-clamp assay (Tyagarajan, et al., *Bioorganic and Medicinal Chemistry Letters* 2010, 20(18), 5536-5540; compound 38 in the paper). Additionally, when orally dosed at 10 mg/kg in a rat spinal ligation model of neuropathic pain, Compound B was significantly more therapeutically efficacious than 3-10 times higher doses of the commercially available sodium channel blockers mexiletene, lamotrigene, and carbamazepine. The structure of Compound B is:

compound B

Compound C has been reported as a Nav 1.7 channel blocker with an $IC_{50}$ value of 20 nM (Chakka et al., Bioorg. Med. Chem. Lett. 2012, 22(5), 2052-2062; compound 32 in the paper). The structure of compound C is:

compound C

All compounds were formulated in a 10% hydroxypropyl-β-cyclodextrin (HPβCD) 1×PBS vehicle. Compounds were prepared as 1% stock solutions in absolute ethanol. An appropriate amount of the stock solution was transferred to a glass vial from which the solvent was evaporated, then the compound was re-suspended in appropriate volumes of vehicle and ball-milled overnight at 4° C. All compounds were tested at 0.01%, 0.1%, 0.3%, and 1% w/v, unless otherwise noted. Alcaine® (Alcon Laboratories, Fort Worth, Tex.) was used as a reference compound.

Rats were dosed with 5 µL, of formalin vehicle (0.9% sterile saline) in OS eye. After a 5-second acclimation period, blinks were counted for one minute. Test compound or vehicle was dosed (5 µL) on OD eye. At 5 minutes after test compound treatment (unless otherwise noted), 0.1% formalin was dosed in the OD eye. Blinks were counted in the same manner as the OS eye.

The efficacy data for these compounds are plotted in FIGS. 1, 3, 4, and 5, with % inhibition of formalin-induced blink rate indicated above the bar for each tested concentration.

It is apparent that Compound 1 was both significantly more potent (a lower concentration is needed to afford a therapeutic effect) and more efficacious (a larger maximum efficacy) as a topical ocular analgesic than the literature Nav 1.7 inhibitors Compounds A and B, (by comparison of FIG. 1 to FIGS. 3 and 4, respectively). even though Compound 1 was reported to have the lowest in vitro potency of the three compounds at the Nav 1.7 channel (reported as 170 nM using whole cell manual patch-clamp assay; *Journal of Medicinal Chemistry* 2011, 54(13), 4427-4445; Compound 1 is compound 52 in the paper), and even though Compound B was disclosed to be therapeutically effective when orally dosed in a rat in vivo pain model. Thus Compound 1 unexpectedly afforded superior performance to literature Nav 1.7 inhibitors A and B, when topically applied to the surface of the eye, in the above-described rat in vivo model of ocular pain. Compound C afforded similar analgesic efficacy to compound 1 when comparing similar dose ranges of 0.05%-0.2% (compare FIGS. 1 and 5).

Example 2

Anesthetic Effects of Compound 1 of Formula I as Compared to Nav 1.7 Inhibitor Compound C Cochet-Bonnet Esthesiometry Test For the Cochet-Bonnet esthesiometry test that measures anesthetic activity, whiskers were trimmed from test animals or vehicle animals. OD eye of animal was dosed with 5 µL of test compound or vehicle. The animal was restrained in a clear plastic cone (DecapiCone®, Alcon Laboratories, Fort Worth, Tex.) which was trimmed as necessary to allow access to the OD eye. Five minutes after application of test compound, a Cochet-Bonnet esthesiometer, with a nylon monofilament diameter of 0.12 mm and length of 40 mm (0.8 g/mm$^2$), was applied perpendicularly to the central cornea of the OD eye 10 times. This test was performed three times on each animal within 2 minutes. Data were expressed as the mean number of blinks elicited from 10 stimuli.

Figure 1:
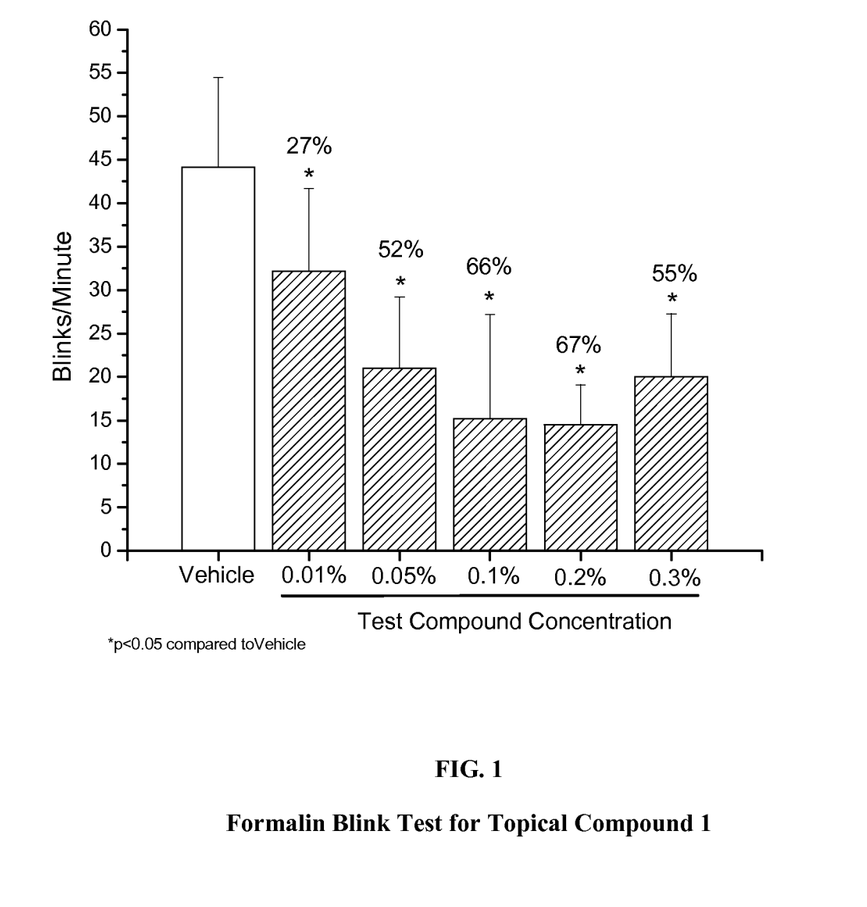
FIG. 1 is a graphical representation of the analgesic efficacy of topical ocular doses of compound 1 in the 0.01%-0.3% w/v range, with respect to reducing the frequency of formalin-induced blinking in rats. Drug concentration is depicted on the x axis, while the number of blinks/minute induced by the formalin+(drug in vehicle or vehicle alone) stimulus is shown on the y axis. The % values above the bars indicate the % reduction of the blink rate for the formalin-challenged, drug-treated animals (at that particular dose) as compared to the formalin-challenged, vehicle-treated animals. Higher % inhibition values=smaller bar heights indicate increased analgesic efficacy. The graph indicates that >50% efficacy was observed at drug concentrations≥0.05% w/v, as compared to vehicle.
Figure 2:
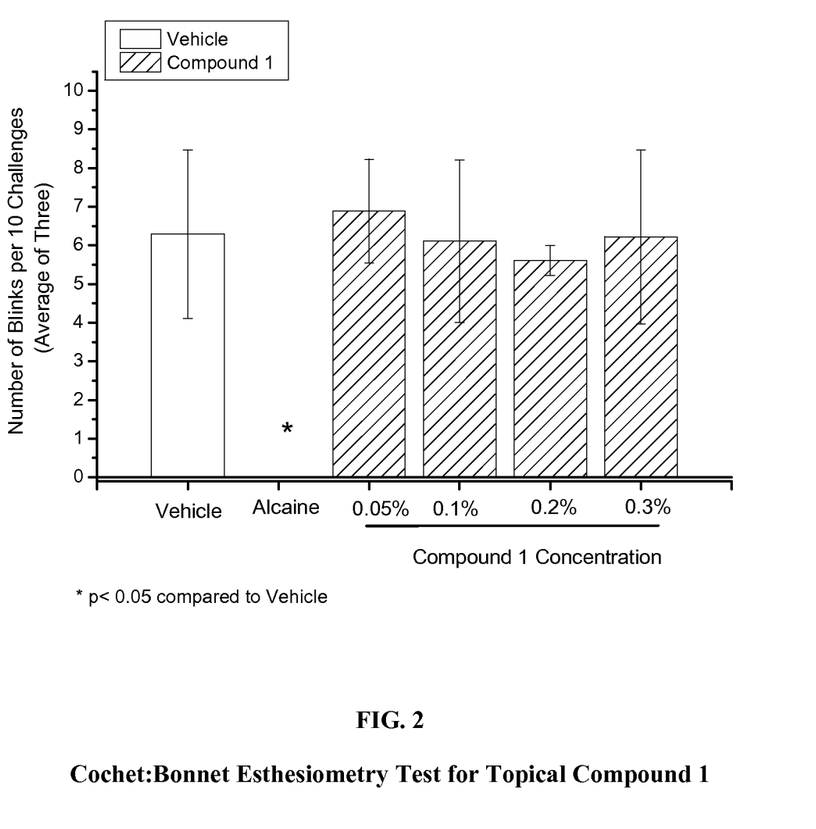
FIG. 2 is a graphical representation of the anesthetic efficacy of topical ocular 0.05-0.3% doses of compound 1, with respect to reducing the frequency of nylon fiber ocular surface touching-induced blinking in rats, as compared to vehicle-treated and Alcaine®-treated animals. Smaller bar heights indicate increased anesthetic efficacy. The graph indicates that drug concentrations up to 0.3% w/v did not elicit a statistically significant anesthetic effect, as compared to vehicle.
Figure 3:
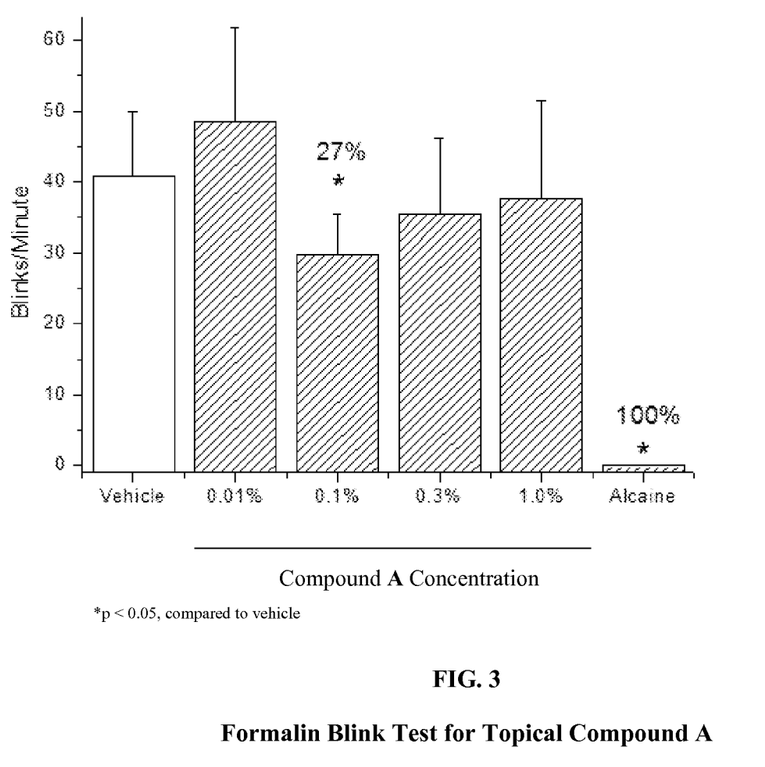
FIG. 3 is a graphical representation of the analgesic efficacy of compound A=1'-pentyl-6H-spiro[[1,3]dioxolo[4,5-f]benzofuran-7,3'-indolin]-2'-one, in the 0.1-1% w/v dose range with respect to reducing the frequency of formalin-induced blinking in rats. The graph indicates that a modest 27% reduction was observed only at the 0.1% dose, and not at the other doses.
Figure 4:
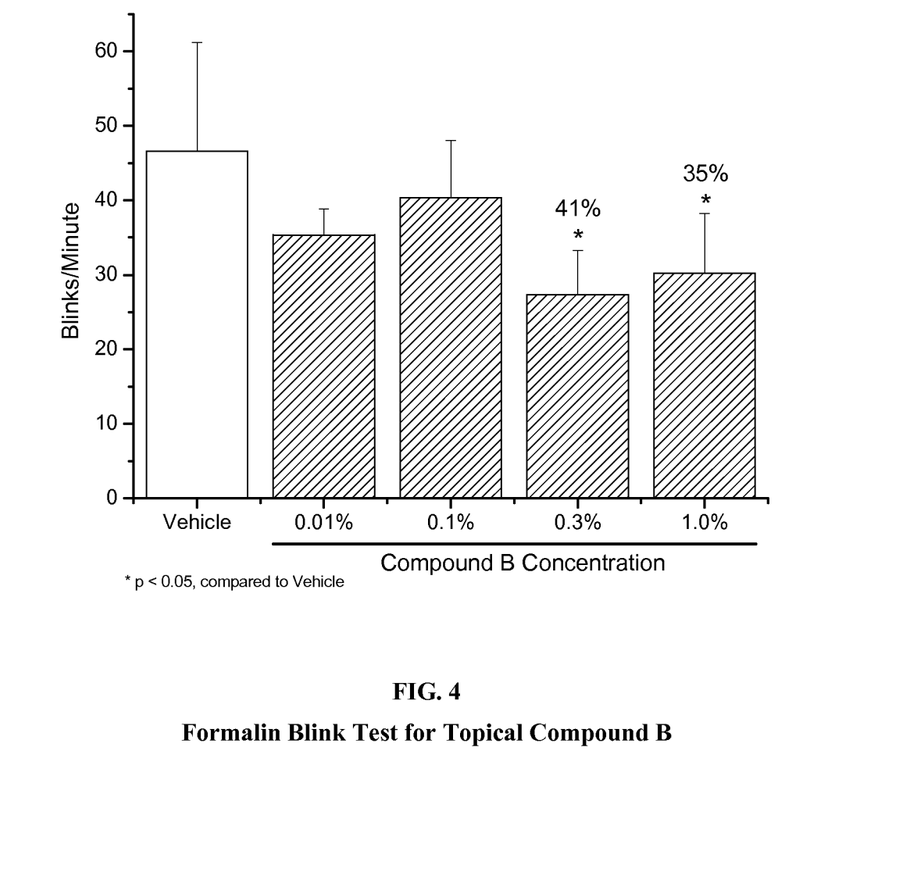
FIG. 4 is a graphical representation of the analgesic efficacy of compound B=4-(2'-(trifluoromethoxy)-[1,1'-biphenyl]-3-yl)thiazole-2-carboxamide, in the 0.1-1% w/v dose range with respect to reducing the frequency of formalin-induced blinking in rats. The graph indicates that no effect was observed at 0.01% and 0.1% doses, with ~40% reduction observed at the 0.3% and 1% doses.
Figure 5:
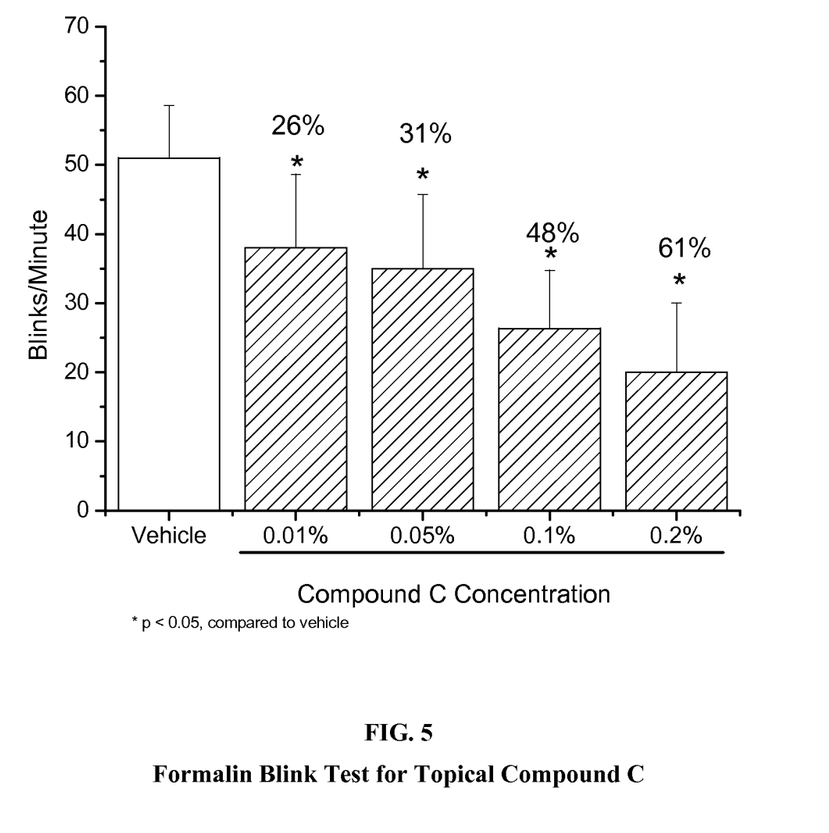
FIG. 5 is a graphical representation of the analgesic efficacy of compound C=4-((7-(2,3-difluorobenzyl)-7H-pyrrolo[2,3-d]pyrimidin-4-yl)oxy)piperidin-1-yl)methyl)thiazole, in the 0.01-0.2% w/v dose range with respect to reducing the frequency of formalin-induced blinking in rats. The graph indicates a dose-related increase in efficacy in this range, with a maximum 61% efficacy observed at the top tested dose.
Figure 6:
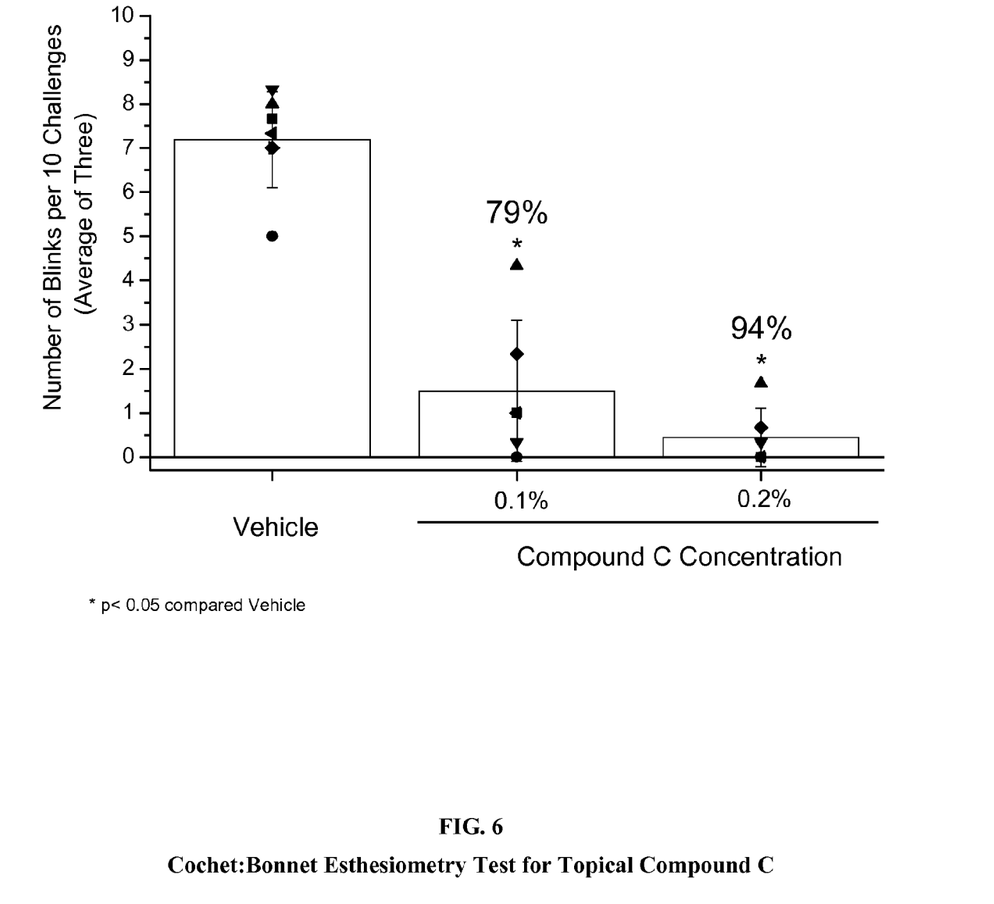
FIG. 6 is a graphical representation of the anesthetic efficacy of topical ocular 0.1% and 0.2% doses of compound C with respect to reducing the frequency of nylon fiber ocular surface touching-induced blinking in rats, as compared to vehicle-treated and Alcaine®-treated animals. The graph indicates that both of these doses elicited significant anesthesia.

Compound 1 of formula 1 and compound C were evaluated in this assay, with the results displayed graphically in FIGS. 2 and 6, respectively. A comparison of these figures demonstrates that while compound 1 did not elicit observable anesthesia over the concentration range that afforded efficacious analgesia in the formalin blink test, compound C afforded profound anesthesia.

The results of these experiments demonstrate that unlike other Nav 1.7 inhibitors reported in the art, a topical formulation of compound 1 of formula I of the present invention uniquely has the desirable profile of affording analgesia without anesthesia, in a rat model of ocular pain.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. A method for the treatment of ocular pain which comprises administering to a patient in need thereof a topical ophthalmic formulation containing a therapeutically effect amount of at least one compound of Formula I wherein:

Y=CH or N;
n=0 or 1, with the proviso that n=0 if Y=N;
X=a direct bond or CH$_2$;
Z=a phenyl or heteroatomic group, optionally substituted with phenyl, methyl; halo, trihalomethyl, or trihalomethoxy; and
R$^2$=H, Me, or F, with the Me or F groups in the 2 or 6 positions on the acetamide-bearing phenyl ring.

2. The method of claim 1, wherein said treatment comprises treatment with any of the following compounds:

-continued

-continued

3. The method of claim 1, wherein the compound of Formula I has the following structure:

4. The method of any of claims 1-3, wherein the topical ophthalmic formulation comprises one or more ingredients selected from the group consisting of surfactants; tonicity agents; buffers; preservatives; co-solvents; and viscosity building agents.

5. The method of claim 1, wherein the therapeutically effect amount of a compound of Formula I is between 0.01-3%.

6. The method of claim 1, wherein the therapeutically effect amount of a compound of Formula I is between 0.1-1%.

7. A topical ocular pharmaceutical composition comprising:
 a cyclodextrin or sodium polystyrene sulfonate; and
 a therapeutically effect amount of compound of Formula I

I wherein:

$R^1$ =

Y=CH or N;
n=0 or 1, with the proviso that n=0 if Y=N;
X=a direct bond or CH$_2$;
Z=a phenyl or heteroatomic group, optionally substituted with phenyl, methyl; halo, trihalomethyl, or trihalomethoxy; and

R²=H, Me, or F, with the Me or F groups in the 2 or 6 positions on the acetamide-bearing phenyl ring.

8. The pharmaceutical composition of claim 7, wherein said composition comprises one or more of the following compounds:

9. The pharmaceutical composition of claim 8, wherein the compound of Formula I has the following formula:

10. The pharmaceutical composition of any of claims 7-9, wherein the topical ophthalmic formulation comprises one or more ingredients selected from the group consisting of surfactants; tonicity agents; buffers; preservatives; co-solvents; and viscosity building agents.

11. The pharmaceutical composition of claim 7, wherein the therapeutically effect amount of a compound of Formula I is between 0.01-3%.

12. The pharmaceutical composition of claim 7, wherein the therapeutically effect amount of a compound of Formula I is between 0.1-1%.

* * * * *